US009021861B2

(12) United States Patent
Ludwig

(10) Patent No.: US 9,021,861 B2
(45) Date of Patent: May 5, 2015

(54) HEATABLE FLOW-THROUGH MEASUREMENT CELL

(75) Inventor: Michael Ludwig, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 274 days.

(21) Appl. No.: 13/379,302

(22) PCT Filed: Jun. 16, 2010

(86) PCT No.: PCT/EP2010/058447
§ 371 (c)(1),
(2), (4) Date: Apr. 16, 2012

(87) PCT Pub. No.: WO2010/146079
PCT Pub. Date: Dec. 23, 2010

(65) Prior Publication Data
US 2012/0192621 A1   Aug. 2, 2012

(30) Foreign Application Priority Data

Jun. 19, 2009 (DE) .......................... 10 2009 029 949

(51) Int. Cl.
*G01N 21/3504* (2014.01)
*G01N 21/05* (2006.01)
*G01N 21/03* (2006.01)
*G01N 21/09* (2006.01)

(52) U.S. Cl.
CPC ............ *G01N 21/05* (2013.01); *G01N 21/0332* (2013.01); *G01N 21/09* (2013.01); *G01N 21/3504* (2013.01)

(58) Field of Classification Search
USPC .......................................................... 73/25.05
See application file for complete search history.

(56) References Cited

U.S. PATENT DOCUMENTS

| 4,205,550 A | 6/1980 | Swanson |
| 4,587,835 A * | 5/1986 | Adams .......................... 73/23.37 |
| 5,223,716 A | 6/1993 | Rossiter |
| 5,424,832 A * | 6/1995 | Nakano et al. ................. 356/312 |
| 6,188,475 B1 * | 2/2001 | Inman et al. ................... 356/246 |
| 6,601,776 B1 * | 8/2003 | Oljaca et al. ....................... 239/5 |
| 2006/0263256 A1 | 11/2006 | Koshel et al. |

FOREIGN PATENT DOCUMENTS

| CN | 101281121 A | 10/2008 |
| EP | 1767922 | 3/2007 |
| GB | 1500740 | 2/1978 |
| JP | 57163845 A | 10/1982 |
| JP | 59035131 | 2/1984 |
| JP | 2002267596 | 9/2002 |
| JP | 2008164304 | 7/2008 |

* cited by examiner

Primary Examiner — Paul West
(74) Attorney, Agent, or Firm — Cozen O'Connor

(57) ABSTRACT

A heatable flow-through measuring cell for a gas analyzer having an inner tube made of a corrosion-resistant material, such as stainless steel, and is terminated at each end with a respective end piece and a radiolucent window held therein. The measuring cell also includes an electrical heating apparatus for heating each end piece, an outer tube that coaxially surrounds the inner tube so as to form a narrow gap and is made of material with good thermal conductivity, such as aluminum, and includes thermal insulation that surrounds the outer tube.

6 Claims, 1 Drawing Sheet

HEATABLE FLOW-THROUGH MEASUREMENT CELL

CROSS-REFERENCE TO RELATED APPLICATIONS

This is a U.S. national stage of application No. PCT/EP2010/058447 filed 16 Jun. 2010. Priority is claimed on German Application No. 10 2009 029 949.1 filed 19 Jun. 2009, the content of which is incorporated herein by reference in its entirety.

BACKGROUND OF THE INVENTION

1. Field of the Invention

The invention relates to measurement cells and, more particularly, to a heatable flow-through measurement cell for a gas analyzer.

2. Description of the Related Art

EP 1 767 922 A2 discloses a flow-through measurement cell comprising a tube, which is terminated at each end with a respective heatable end piece and a radiolucent window held therein. The measurement gas is supplied at one end of the tube and discharged at the other, or is preferably supplied in the center of the tube and discharged at both ends of the tube.

U.S. Pat. No. 4,205,550 discloses a flow-through measurement cell comprising an inner tube that is made of steel or aluminum and is terminated at each end with a respective end piece, which is provided with cooling fins, and a radiolucent window held therein. The inner tube is surrounded coaxially by an outer tube made of steel or aluminum such that a gap is formed. Each tube contains openings that lie diametrically opposite one another, where the passage of combustion gases to be analyzed through the measurement cell is enabled or blocked depending on the rotated position of the outer tube with respect to the inner tube.

JP 59-035 131 AA discloses a flow-through measurement cell that is made of glass and is integrated in a heatable metal block with the inclusion of a thermally conductive material that absorbs different thermal expansions, such as silver solder.

JP 57-163 845 AA likewise discloses a through-flow measurement cell that is integrated in a heatable metal block.

In contrast to in-situ gas analysis, extractive gas analysis involves extracting the gas to be analyzed from a process and conducting the extracted gas through a flow-through measurement cell, where it is analyzed by spectroscopy, non-dispersive infrared (NDIR) lasers, etc. Here, it is often necessary to take measurements at higher temperatures to prevent condensation of water in the extraction lines and the measurement cell or undesirable reactions. The measurements can be taken at temperatures of up to 200° C. using a heated measurement cell. The measurement result is dependent on the temperature of the measurement gas. As a result, the temperature of the measurement gas along the measurement section formed by the measurement cell has to be location-independent to within a few Kelvin.

In order to achieve the required temperature resistance and corrosion resistance, i.e., in the case of aggressive measurement gases, the material typically used for the inner wall of the measurement cell is high-grade steel. High-grade steel has a thermal conductivity that is relatively low for metals, however, and therefore undesirable temperature gradients can arise when heating the measurement cell, i.e., in the case of elongated measurement cells in the order of magnitude of one meter. To date, the formation of temperature gradients has been reduced, for example, by the uniform application of heating tapes to the outer side of the measurement cell, and also if appropriate by breaking the heating down into a plurality of heating circuits that are controlled separately. It is also known to arrange the measurement cell in a circulating air furnace, which makes uniform heating possible.

The expenditure in terms of instrumentation or apparatus associated with the known solutions is relatively high, however.

SUMMARY OF THE INVENTION

It is therefore an object of the invention to reduce instrumentation or the required apparatus associated with known solutions for a measurement cell. This and other objects an advantages are achieved in accordance with the invention by providing a heatable flow-through measurement cell for a gas analyzer, comprising an inner tube that is made of corrosion-resistant material and is terminated at each end with a respective end piece and a radiolucent window held therein, each having an electrical heating apparatus for heating the end pieces, comprising an outer tube that is made of material with good thermal conductivity and surrounds the inner tube coaxially so as to form a narrow gap, and comprising thermal insulation that surrounds the outer tube, where the heating apparatuses are integrated in the end pieces or abut against the outside of the end pieces.

In accordance with the invention, the inner tube forms the corrosion-resistant inner wall of the measurement cell and consists of a material that is corrosion-resistant with respect to the measurement gas, such as high-grade steel, tantalum, polytetrafluoroethylene (PTFE) or a carbon fiber composite material (carbon). Such materials have a relatively low thermal conductivity. In conjunction with the thermal insulation lying thereon, the outer tube, which consists of a material with good thermal conductivity, such as aluminum or copper, ensures that there is a uniform distribution of heat in the axial direction, such that no considerable temperature gradient can form over the length of the inner tube. It therefore suffices to heat the tubular measurement cell merely at the ends, and therefore only two heating apparatuses are required. These are integrated in the end pieces that terminate the inner tube at both ends and are provided with windows, or abut against the end pieces from the outside. The gas connections required for supplying and discharging the measurement gas can be provided directly on the inner tube in the region of the ends thereof or in the end pieces. It is also possible, for example, for the measurement gas to be supplied via a gas connection in the center of the tube and to be discharged in both end regions.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For a more detailed explanation of the invention, reference is made hereinbelow to the drawing, in which.

DETAILED DESCRIPTION OF THE PREFERRED EMBODIMENTS

Figure 1:
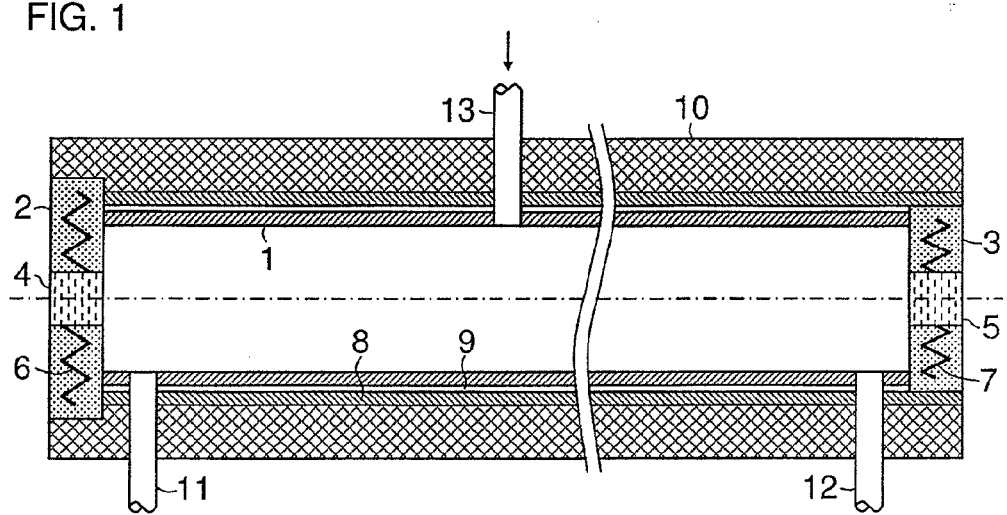
FIG. 1 shows a first exemplary embodiment in accordance with the invention.

FIG. 1 shows a flow-through measurement cell for a gas analyzer (not shown here). The measurement cell consists of an inner high-grade steel tube 1, which is terminated at the ends thereof with two end pieces 2, 3 made of the same or a different corrosion-resistant material. Each of the two end pieces 2, 3 comprises a radiolucent window 4 and an electrical heating apparatus 6, 7. The heating apparatus 6, 7 can also be mounted on the outside of the respective end piece 2, 3. The high-grade steel tube 1 is surrounded coaxially by an outer aluminum or copper tube 8 which, as shown in the left-hand half of FIG. 2 using the example of the end piece 2, is held between the end pieces 2, 3 or, as shown in the right-hand half of FIG. 2 using the example of the end piece 3, rests on the end pieces 2, 3. In order to obtain a long measurement section and to simultaneously minimize the flow-through volume of the measurement cell, the length-to-diameter ratio of the high-grade steel tube 1 is greater than 10 (e.g., diameter 4 cm, length 100 cm). A gap 9 is provided between the two tubes 1 and 8 to account for manufacturing tolerances and different thermal expansions of the tubes 1 and 8. The gap 9 is dimensioned such that sufficient thermal coupling of the high-grade steel tube 1 with relatively poor thermal conductivity to the aluminum or copper tube 8 with relatively good thermal conductivity is brought about by the thermal conductivity of a gas (e.g., air) or other material (e.g., a thermally conductive paste) located in the gap. Thermal insulation 10 is applied to the aluminum or copper tube 8 and is designed such that the influence of the ambient temperature on the aluminum or copper tube 8 remains below predefined limits.

Figure 2:
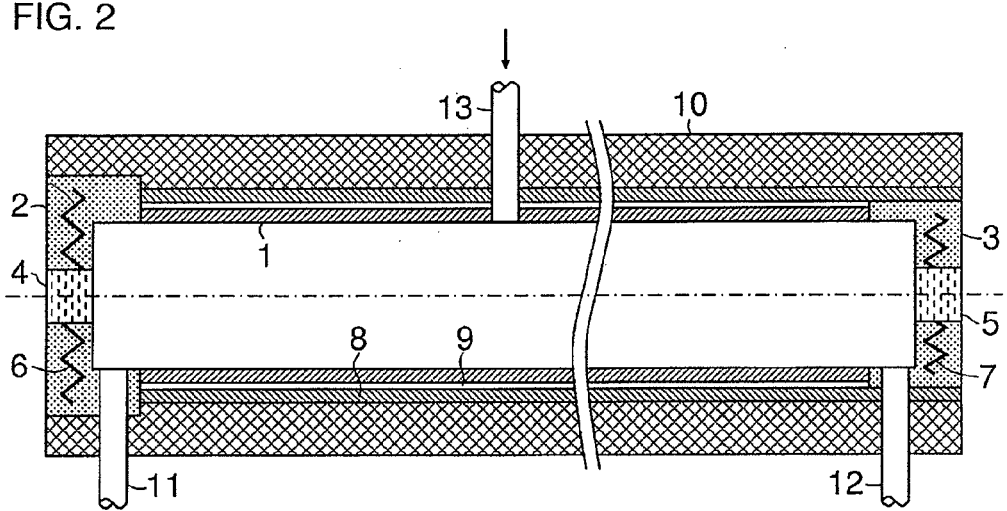
FIG. 2 shows a further exemplary embodiment of the flow-through measurement cell in accordance with the invention.

In accordance with the illustration in FIG. 1, the gas connections 11, 12 required for supplying and discharging the measurement gas can be arranged directly on the high-grade steel tube 1 in the region of the ends thereof, or, as shown in FIG. 2, in the end pieces 2, 3. It is also possible for the measurement gas to be supplied through a gas connection 13 located in the center of the tube and to be discharged through the gas connections 11, 12 in both end regions.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A heatable flow-through measurement cell for a gas analyzer, comprising:
    an inner tube comprising a corrosion-resistant material, the inner tubing being terminated at each end with a respective end piece and a radiolucent window held therein, each radiolucent window having an electrical heating apparatus for heating the respective end piece;
    a single outer tube comprising a material with good thermal conductivity, the single outer tube surrounding substantially an entire length of the inner tube coaxially so as to form a narrow gap extending between the single outer tube and the entire length of the inner tube; and
    thermal insulation surrounding the single outer tube;
    wherein the heating apparatus of each respective end piece is integrated in a respective end piece or abuts against an outside of the respective end piece; and
    wherein the single outer tube is held between the respective end pieces or rests on the respective end pieces.

2. The heatable flow-through measurement cell as claimed in claim 1, wherein the inner tube consists of one of the following materials: high-grade steel, tantalum, polytetrafluoroethylene (PTFE) and carbon fiber composite material.

3. The heatable flow-through measurement cell as claimed in claim 2, wherein the single outer tube consists of one of the following materials: aluminum and copper.

4. The heatable flow-through measurement cell as claimed in claim 1, wherein the single outer tube consists of one of the following materials: aluminum and copper.

5. The heatable flow-through measurement cell as claimed in claim 1, further comprising:
    a respective gas connection in a region of each end of the inner tube thereof.

6. The heatable flow-through measurement cell as claimed in claim 1, further comprising:
    a gas connection in the respective end piece.

* * * * *